(12) United States Patent
Oltarshevskaya et al.

(10) Patent No.: US 9,011,901 B2
(45) Date of Patent: Apr. 21, 2015

(54) METHOD OF PROMOTING HEMOSTASIS BY USING A DRESSING COMPRISING EXTRACT OF CHAMOMILE AND NETTLE

(71) Applicant: Linda Eastwood, Beverly Hills, CA (US)

(72) Inventors: Natalia Dmitrievna Oltarshevskaya, Moscow (RU); Larisa Borisovna Savilova, Moscow (RU); German Evseevich Krichevsky, Moscow (RU)

( * ) Notice: Subject to any disclaimer, the term of this patent is extended or adjusted under 35 U.S.C. 154(b) by 267 days.

(21) Appl. No.: 13/720,307

(22) Filed: Dec. 19, 2012

(65) Prior Publication Data

US 2013/0108684 A1 May 2, 2013

Related U.S. Application Data

(63) Continuation of application No. 13/243,780, filed on Sep. 23, 2011, now Pat. No. 8,349,356, which is a continuation of application No. 11/793,339, filed as application No. PCT/IB2004/004355 on Dec. 20, 2004, now abandoned.

(51) Int. Cl.

| A61F 13/00 | (2006.01) |
|---|---|
| A61K 36/28 | (2006.01) |
| A61K 36/185 | (2006.01) |
| A61L 15/16 | (2006.01) |
| A61L 15/40 | (2006.01) |
| A61K 31/722 | (2006.01) |
| A61K 45/06 | (2006.01) |

(52) U.S. Cl.
CPC ............ *A61K 36/28* (2013.01); *A61K 2300/00* (2013.01); *A61F 13/00* (2013.01); *A61K 31/722* (2013.01); *A61K 36/185* (2013.01); *A61K 45/06* (2013.01); *A61L 15/40* (2013.01); *A61L 2400/04* (2013.01)

(58) Field of Classification Search
None
See application file for complete search history.

(56) References Cited

U.S. PATENT DOCUMENTS

| 4,393,048 A | 7/1983 | Mason, Jr. et al. |
|---|---|---|
| 4,658,839 A | 4/1987 | Dallal et al. |
| 4,673,568 A | 6/1987 | Grollier et al. |
| 2003/0129183 A1 | 7/2003 | Spillert et al. |

FOREIGN PATENT DOCUMENTS

| RU | 2 040 252 C1 | 7/1995 |
|---|---|---|
| RU | 2063246 C1 | 7/1996 |
| RU | 2101033 C1 | 1/1998 |
| RU | 2157243 C1 | 10/2000 |
| RU | 2179428 C2 | 2/2002 |

OTHER PUBLICATIONS

International Search Report for PCT/IB2004/004355, 1 page (Sep. 15, 2005).
Iso et al., Solution Properties of Sodium Alginate from Brown Seaweecis Living along the Coast of Japan—II, Bull. Jap. Soc. Scientific Fisheries, 44(12):1375-1379 (1978).
Sodium Alginate website (http://www.clubnatural.com/alginate.html) accessed Jul. 20, 2010.
Soni et al., Evaluation of the health aspects of methyl paraben:a review of the published literature, Food Chem. Toxicol., 40(10):1335-1373 (2002).
International Preliminary Report on Patentability (Chapter I) for PCT/IB04/04355, mailed Sep. 15, 2005.

*Primary Examiner* — Kevin S Orwig
(74) *Attorney, Agent, or Firm* — Choate, Hall & Stewart, LLP; Brenda Herschbach Jarrell; Elizabeth M. Rohlfs

(57) ABSTRACT

The present invention provides hemostatic compositions comprising components of the flowers of pharmaceutical chamomile (*Chamomilla recutita*) and the leaves of dioecious nettle (*Urtica dioica*). Further inclusion of a biocompatible polymeric base, particularly an alignate, generates a composition with excellent and broad spectrum hemostatic capabilities, with concurrent antiseptic and anti-inflammatory properties. The invention further provides methods of using the inventive compositions in to reduce or stop bleeding, as well as a variety of apparatuses useful in hemostatic contexts that incorporate the inventive compositions. In one particular embodiment, the invention provides hemostatic dressings in which a polymeric layer incorporating chamomile and nettle components is applied to a textile or fabric material, for example a non-woven viscose.

36 Claims, No Drawings

METHOD OF PROMOTING HEMOSTASIS BY USING A DRESSING COMPRISING EXTRACT OF CHAMOMILE AND NETTLE

CROSS-REFERENCE

The present application is a continuation of prior filed application Ser. No. 13/243,780, filed Sep. 23, 2011, now U.S. Pat. No. 8,349,356, which is a continuation of prior filed application Ser. No. 11/793,339, filed Jun. 18, 2007, now abandoned, which was the National Stage of International Application No. PCT/IB2004/004355, filed Dec. 20, 2004, the contents of each of which are incorporated by reference herein.

BACKGROUND

A wide variety of compositions and devices have been developed for use in controlling bleeding. However, available compositions and dressings typically have only a modest hemostatic effect, so that bleeding continues for several (e.g., 2-3 minutes or more) after application of composition or dressing. Additionally, many dressings have only modest antiseptic abilities. Also, typical dressings are prepared from materials that have a tendency to adhere to the injured surface, causing significant pain to the patient when the dressing is applied or removed. Because of the modest hemostatic and/or antiseptic activity, standard dressings often need to be changed frequently, further exacerbating adhesion problems.

There remains a need for the development of improved hemostatic compositions, methods, and devices.

SUMMARY OF THE INVENTION

The present invention provides improved compositions with antiseptic and properties. The invention encompasses the recognition that certain combinations of components of the flowers of pharmaceutical chamomile (*Chamomilla recutita*) and the leaves of dioecious nettle (*Urtica dioica*) produce highly effective hemostatic compositions. Further inclusion of a biocompatible polymeric base, particularly an alignate, generates a composition with excellent and broad spectrum hemostatic capabilities, with concurrent antiseptic and anti-inflammatory properties.

The invention further provides methods of using the inventive compositions in order to reduce or stop bleeding and/or to treat wounds or burns, as well as a variety of apparatuses useful in hemostatic contexts that incorporate the inventive compositions. In one particular embodiment, the invention provides hemostatic dressings. This embodiment is exemplified herein with a layered textile device comprising a textile layer and a polymeric layer incorporating chamomile and nettle components.

DETAILED DESCRIPTION OF CERTAIN PREFERRED EMBODIMENTS OF THE INVENTION

Hemostatic Compositions

As described above, the present invention provides hemostatic compositions containing specified amounts of chamomile and nettle components. Desirably, these compositions further contain a biocompatible polymer or gel, e.g., an alginate. Alternatively or additionally, inventive hemostatic compositions may contain other pharmaceutical agents.

Chamomile and Nettle

The present invention provides hemostatic compositions containing chamomile and nettle components. According to the present invention, combinations of chamomile and nettle components make it possible to noticeably increase the hemostatic properties of the nettle components without decreasing the antiseptic properties of the chamomile components.

In some embodiments, the inventive compositions contain chamomile components and nettle components in a ratio within the range of about 0.2-5.0:1.0 by weight of chamomile flowers to nettle leaves. In some embodiments, this ratio is within the range of about 1.0-3.0 chamomile flowers to nettle leaves.

As described in Example 1, for example, chamomile and nettle components may be provided as an extract of chamomile and nettle plants. In some embodiments, a chamomile extract is prepared from chamomile flowers; in some embodiments, a nettle extract is prepared from nettle leaves. Chamomile and nettle extracts may be prepared separately and then combined, or alternatively chamomile and nettle plant portions may first be combined together (before or after grinding), so that a single extract is prepared from the combination.

Example 1 describes preparation of an aqueous extract of chamomile flowers and nettle leaves. Those of ordinary skill in the art will readily appreciate that alternative extraction strategies (e.g., alcohol extraction) may alternatively be employed, so long as appropriate chamomile and nettle active components are obtained. Similarly, those of ordinary skill in the art will appreciate that appropriate chamomile and nettle components may be provided by techniques other than extraction; indeed, in some cases it may be possible to obtain isolated components from commercial sources.

However the chamomile and nettle components are obtained, they are desirably combined in amounts appropriate based on the above-noted weight ratios for chamomile flowers and nettle leaves. For example, if individual isolated components (e.g., discrete chemical compounds) or other component preparations are obtained, they are desirably combined with one another to achieve individual component amounts that would be present had chamomile flowers and nettle leaves been mixed at the indicated weight ratios, as described above and in Example 1.

Chamomile flowers (fresh or dried), water, and oil can be obtained from any of a variety of commercial sources (e.g., Artemis herbs), or can be prepared according to known techniques. The flowers of chamomile contain about 1-2% volatile oils including alpha-bisabolol, alpha-bisabolol oxides A & B, and matricin (usually converted to chamazulene during hot water extraction or steam distillation). Other components include the flavonoids apigenin, luteolin, and quercetin. Bitter glycosides (anthemic acid), coumarins (including umbelliferon and herniarin), phenolic carboxylic acids, polysaccharides, mucilage, choline, amino acids, tannins, and malic acid.

Nettle plants or leaves can be obtained fresh or dried from a variety of commercial sources, as can various extracts. Techniques for cultivating and processing nettle are also well known in the art. Nettle is known to contain amines, including histamine, formic acid, serotonin, flavonoids (including rutin and quercitrin), glycocides, tannins, carotenes, and vitamin C, among other components.

Biocompatible Polymer or Gel

Inventive compositions comprising chamomile and nettle components may optionally include one or more additional components. In many instances, it will be desirable to include a biocompatible polymer or gel, for example to localize and impart a useful consistency to the composition. A variety of biocompatible polymers are known in the art.

In certain embodiments, the biocompatible polymer comprises agarose, agar, carrageen, alginic acid, alginate and/or other alginic acid derivatives, hyaluronic acid and/or hyaluronate derivatives, polyanionic polysaccharides, chitin, chitosan, fibrin, polyglycolide, polylactide, polycaprolactone, dextran and/or copolymers thereof, polyvinyl pyrrolidone, polyacrylates, waxes, polyethylene-polyoxypropylene-block polymers, wool fat, poly(L-lactic acid), poly(DL-Lactic acid) copoly(lactic/glycolic acid), cellulose and/or its derivatives such as sodium carboxymethyl cellulose, ethyl cellulose and/or cellulose acetate, glycols such as propylene glycol or polyethylene glycol, polylactide-polyglycolide, polymethyldisiloxane, polycaprolactone, polylactic acid, ethylene vinyl acetate, or combinations thereof.

In some embodiments, the biocompatible polymer comprises a hydrophilic polymer. Useful hydrophilic polymers include, for example, hydrophilic diols, hydrophilic diamines, and combinations thereof. Hydrophilic diols can be, for example, poly(alkylene)glycols, polyester-based polyols, polycarbonate polyols, or combinations thereof. As used herein, the term "poly(alkylene)glycol" refers to polymers of lower alkylene glycols such as poly(ethylene)glycol, poly(propylene)glycol polytetramethylene ether glycol (PT-MEG), and combinations thereof.

Biocompatible polymers for use in accordance with the present invention may be or include a hydrogel, such as, for example, a copolymer or block-polymer or the like. Useful hydrogels include crosslinked keratin, polymethylmethacrylate, polyethylene glycol, polyalkoxyalkyl (meth)acrylate, ethylene/vinylalcohol copolymer, polyurea, a polyurethane polyurethane/polyurea, and combinations thereof, to name but a few.

In addition to providing useful localization and retention attributes to the inventive hemostatic compositions, polymers or gels that attract, absorb, or otherwise incorporate water may have additional advantages, including, for example, an ability to promote coagulation, and therefore may be particularly useful in the practice of the present invention. To give but one example, alginate can enhance the hemostatic properties of compositions according to the present invention.

The amount of biocompatible polymer or gel utilized in accordance with the present invention will be selected to permit or achieve the desired hemostatic results. In some embodiments, chamomile/nettle components will be present at an amount within a range of about 0.3 to 0.9% of the amount by weight of biocompatible polymer or gel. In some embodiments, the amount will be within a range of about 0.4 to 0.6% by weight; in some embodiments the amount will be within a range of about 0.5-0.55%. Some embodiments contain 0.33-0.92% chamomile/nettle components by weight in an alginate composition; others contain 0.5-0.55% chamomile/nettle components by weight in alginate. This weight relationship makes it possible to effectively increase the coagulability of blood, preserve hugh antiseptic and antiinflammatory properties, and, at the same time, maintain sufficient viscosity in the wound to facilitate clotting, which, in the final analysis, influences the speed with which bleeding is halted.

Pharmaceutical Agent

Those of ordinary skill in the art will readily appreciate that it may sometimes be desirable to include one or more additional pharmaceutical agents, in addition to the chamomile and nettle components, in the hemostatic compositions of the present invention.

For example, the composition of the present invention optionally includes one or more of an antimicrobial, an antibiotic, an antimyobacterial, an antifungal, an antiviral, an antioxidant, an antineoplastic agent, an agent affecting the immune response, an antithrombotic, an antihyperlipidemic agent, a cardiac drug, a thyromimetic or antithyroid drug, an adrenergic, an antihypertensive agent, a cholinergic, an anticholinergic, an antispasmodic, an antiulcer agent, a skeletal and/or smooth muscle relaxant, a prostaglandin, a general inhibitor of the allergic response, an antihistamine, a local anesthetic, an analgesic, a narcotic antagonist, an antitussive, a non-steroidal anti-inflammatory agent, a steroidal anti-inflammatory agent, an antioxidant, a vaso-active agent, a bone-active agent, an antiarthritic, a vitamin, or a diagnostic agent.

In certain embodiments, the composition optionally includes one or more of an antimicrobial, an antibiotic, an antimyobacterial, an antifungal, an antiviral, a local anesthetic, an analgesic, an antioxidant, an antiseptic agent, a vitamin, or combinations thereof.

Just to give a few examples, particular antimicrobial compounds that may be useful in the practice of the present invention include, for example, aminoglycosides (e.g., amikacin, gentamicin, tobramycin, and combinations thereof), amoxicillin (with or without clavulanate), amphotericin, ampicillin (with or without sulbactam), azithromycin, aztreonam, bacitracin, cefazolin, cefepime, cefotaxime, cefotetan, cefpodoxime, ceftazidime, ceftizoxime, ceftriaxone, cefuroxime, cephalexin, cephalosporins, chloramphenicol, ciprofloxacin, clarithromycin, clindamycin, clotrimazole, dapsone, dicloxacillin, doxycycline, erythromycin, fluconazole, furazidine (with or without sodium chloride), furazolidone, gatifloxacin, gentamycin, imipenem/cilastatin, isoniazid, itraconazole, kanamycin, ketoconazole, metronizadole, minocycline, nafcillin, neomycin, nitrofural, nitrofuratonin, nystatin, ofloxacin, penicillin, pentamidine, piperacillin, polymyxin, rifampicin, quinupristin, streptomycin, tetracycline, ticarcillin, trimethoprim, vancomycin, etc. Natural antimicrobials such as, for example, propolis, may also be employed. Combinations of such antimicrobial agents may also be employed.

Examples of particular analgesics useful in accordance with the present invention include, for instance, morphine sulfate, codeine sulfate, meperidine, and nalorphine, or combinations thereof.

Examples of particular anesthetics useful in accordance with the present invention include, for instance, procaine, lidocain, tetracaine and dibucaine, or combinations thereof.

In certain embodiments, the inventive hemostatic compositions include one or more pharmaceutical agents selected from the group consisting of chlorhexidine (an antiseptic), furazidine, propolis, mexidole, dimexide (i.e., DMSO), hydrogen peroxide, saline, epinephrine and combinations thereof.

The amount of additional therapeutic agent present in the compositions of this invention will typically be no more than the amount that would normally be administered in a composition comprising that therapeutic agent as the only active agent. In certain embodiments, the amount of additional therapeutic agent in the inventive compositions will range from about 50% to 100% of the amount normally present in a composition comprising that agent as the only therapeutically active agent.

Uses of the Inventive Hemostatic Compositions

The compositions, of the present invention are useful as hemostatic agents. Accordingly, the present composition is useful for controlling, lessening the severity of, or stopping bleeding, for promoting cellular adhesion, or for treatment of an injury such as the site of a wound or accidental injury, an opening incised during a surgical operation, or a puncture site remaining open after removing, for example, a catheter or dialysis needle. Thus, one aspect of the present invention relates to a method for controlling or lessening the severity of bleeding. In some embodiments, the bleeding is associated with a wound or other accidental injury, a dental procedure, or a surgical procedure. Inventive compositions, methods, and devices are useful to treat, for example, dental bleeding, nasal bleeding, bleeding by hemophiliacs, bleeding associated with accidental cuts or abrasions (e.g., as occur in shaving, handling papers, playing games, etc.), wounds, surgical incisions, and other surface bleeding or injury.

The inventive compositions are also useful in the treatment of burns or other wounds (e.g., necrotic trophic ulcers, diabetic foot syndrome, etc.). Arresting haemorrhage from a wound bed can minimize scar formation or other damage. In some embodiments of the inventive compositions useful for treatment of burns or other wounds, epinephrine is included in the compositions. Alternatively or additionally, various antimicrobial and/or antiseptic agents may be included. In some embodiments, one or more of chlorhexidine, furazidine, propolis, mexidole, are included. Particularly useful agents for inclusion in inventive compositions for the treatment of burns include hyaluronic acid, propolis, and/or papaya. In some embodiments, a dressing for minor burns is prepared using a non-woven textile to which a composition is applied, where the composition includes chamomile and nettle components, a biocompatible polymer (e.g., alginate and/or hyaluronic acid), and an additional therapeutic agent (e.g., propolis and/or papaya).

Those of ordinary skill in the art will readily appreciate any of a number of other desirable applications or uses for inventive compositions and devices.

Inventive compositions are delivered or applied to a site of bleeding (or other damage) and are maintained in contact with the site, optionally with light pressure (e.g., applied manually or my means of an adhesive or elastic bandage), for a period of time to reduce or eliminate bleeding. As described below in Example 3, compositions of the present invention have been tested in clinical settings to assess their hemostatic capabilities, and were found to reduce or inhibit bleeding from small vessels such that bleeding was stopped in less than a minute. Thus, according to some embodiments, the invention provides compositions, devices, and methods that, stop bleeding in less than a minute. In some embodiments, bleeding is stopped in less than about, 50, 40, 30, 20, or 10 seconds. In some embodiments, bleeding is stopped within 30-40 seconds. In other embodiments, inventive compositions or devices may be kept in contact with a damaged site for several minutes, or hours, or even days, optionally with one or more changes during the period.

It will also be appreciated that the compositions of the present invention can be employed in combination therapies. That is, the compositions can be, administered concurrently with, prior to, or subsequent to, one or more other desired therapeutic agents or medical procedures. The particular combination of therapies (therapeutic agents or procedures) to employ in a combination regimen will take into account compatibility of the desired therapeutic agents and/or procedures and the desired therapeutic effect to be achieved. It will also be appreciated that the therapies employed may achieve a desired effect for the same disorder (for example, the present composition may be administered concurrently with another agent used to treat the same disorder), or they may achieve different effects (e.g., control of any adverse effects).

Formulations and Devices Including the Inventive Hemostatic Compositions

As will be appreciated by those of ordinary skill in the art, the inventive hemostatic compositions may desirably be incorporated into any of a variety of formulations or devices for topical or transdermal administration.

For example, inventive hemostatic compositions may be formulated as ointments, pastes, creams, lotions, gels, powders, solutions, sprays, or inhalants. In certain embodiments, as discussed above, the hemostatic compositions are incorporated in or on a gel.

Alternatively or additionally, the hemostatic compositions may be applied onto or incorporated within a surface, device, or material that is used to deliver the composition to a wound site. To give but a few non-limiting examples, the compositions may be applied to the surface of a cotton swab or other elongated device for application to a wound, or may be coated on or encased within a flexible surface that can be used to cover, in whole or in part, a wound. In certain embodiments of the invention, the composition is applied to or incorporated into a dressing, such as a bandage or patch, for application to the surface of a wound.

In general, a dressing according to the present invention will include a material onto which the inventive composition is applied. The composition may be localized to only a portion of the material, or may substantially cover a material surface.

In general, the thickness with which the inventive hemostatic composition is applied to a material will be selected to ensure delivery of an adequate amount of composition to promote the mechanical formation of a clot. In some embodiments of the invention, it is desirable that the composition be applied to a material with a thickness not less than about 0.05, 0.04, 0.03, or 0.02 mm. In some embodiments, the composition is applied with a thickness not less than 0.025 mm. In some embodiments, the composition is applied with a thickness of 0.3 mm.

An inventive dressing may also include an attachment means, such as an adhesive, an elastic bandage, a tie, or other means, allowing the dressing to be secured to the site of a wound. In some embodiments, the dressing will include an adhesive substrate (e.g., a plastic or other flexible material with an adhesive surface) whose adhesive surface is partially covered by a fabric material to which an inventive hemostatic composition has been applied.

Desirable materials onto which inventive compositions are applied include any fabric, textile or other material compatible with the composition and its intended use. In some embodiments, it is desirable a gas-permeable material, for example to limit "hothouse" effects underneath a dressing. In some embodiments, it is desirable to employ an absorptive material, for example to remove liquid (particularly aqueous liquids such as blood or water) from a wound site. Such absorptive characteristics may, in some cases, enhance the healing capabilities of inventive dressings, for example by promoting coagulation.

The materials for use in accordance with this aspect of the present invention include woven and non-woven materials. In some embodiments of the invention, non-woven materials are employed. For example, non-woven materials based on cellulose fibers, such as cellulose or viscose cotton, may be employed. In some embodiments, a material comprising viscose fibers is used.

In some embodiments of the invention, particularly those utilizing non-woven materials, the material is stitched with reinforced thread. Such stitching can enhance the stability of the material, and in particular can minimize the risk of material fibers falling into the wound. Rows of stitching may be spaced apart from each other by a distance that is desirably less than about 10 mm. In some embodiments, stitched rows are separated by more than about 1 mm. In other embodiments, stitched rows are separated by about 2, 3, 4, or 5 mm. In some embodiments, stitched rows are separated by 4.0 mm. Often it will be desirable for rows to be evenly spaced. Those of ordinary skill in the art will readily appreciate, however, that irregular spacing is also contemplated by and encompassed within the present invention.

Materials to which inventive compositions are or have been applied may be cut or otherwise formed into any desirable shape. In some embodiments, square, rectangular, circular, or oval-shaped "pads" may be desirable. In other cases, it may be useful to cut or otherwise adjust a device's size to accommodate dimensions of a particular site or wound. Those of ordinary skill in the art will readily appreciate that a wide range of different sizes and shapes of devices is encompassed within the scope of the present invention.

Inventive dressings and other devices may optionally be sterilized and packaged, as is known in the art. For example, sterilization may be accomplished by subjecting a packaged composition or device to radiation, for example gamma radiation or E-beam, or by treatment with ethylene oxide. In some embodiments, inventive compositions or devices are packaged in packaging that is selected and arranged to facilitate removal of a sterile composition or device without contamination. In some embodiments, the packaging is waterproof, for example comprising aluminum foil, plastic, or other conventional material that is easily sterilized. In other embodiments, the packaging is not waterproof, for example comprising paper.

Example 2 below describes one particular embodiment of an inventive dressing. As described, an inventive chamomile/nettle composition is formulated with a biocompatible polymer and applied to the surface of a textile or fabric material. As described in Example 2, the composition is applied evenly across substantially the entire surface of the material; those of ordinary skill in the art will readily appreciate that localized application, and/or application of composition in areas of differing thickness, are also within the scope of the present invention. In some embodiments, however, uniform distribution of composition on the material may have an additional advantage of maintaining a desired and effective amount of hemostatic composition in contact with the wound for an extended period of time.

EXAMPLES

Example 1

Preparation of an Inventive Chamomile/Nettle/Alginate Hemostatic Composition

The present Example describes preparation of an exemplary chamomile/nettle/alginate hemostatic composition according to the present invention.

3.55 g of pharmaceutical chamomile flowers and 1.3 g of dioecious nettle leaves are ground in a mill to a powdery consistency. 200 ml of hot, distilled water are poured over the mixture, and it is boiled for 15 minutes. The mixture is then cooled to a temperature of 40° C. and filtered. The volume of the herbal extract thus obtained is then reduced to 200 ml. 8.3 g of an alginate of sodium is added, and the mixture is maintained at room temperature for 12 hours, with occasional stirring.

Example 2

Layered Textile

The present Example describes preparation of a layered textile in which a chamomile/nettle/alginate composition prepared according to Example 1 is layered on a textile material. The resulting layered textile has long-acting high hemostatic and antiseptic properties, is atraumatic, and displays good sanitary and hygenic properties.

A chamomile/nettle/alginate composition prepared according to Example 1 is evenly applied onto an 80×80 cm layer of non-woven material made of a combination of viscose and cotton fibers stitched with reinforcing thread in rows spaced in 4 mm intervals, so that 120 g of composition are applied per square meter of material. The resulting layered textile is air-dried, cut into 6×10 cm or 10×18 cm pads, packed into paper envelopes laminated in polyethylene, and subjected to sterilization by radiation at a dosage of no more than 15 kiloherz.

Application of the layered textile prepared according to this Example as a Wound dressing is atraumatic as the side with the biocompatible polymer is applied to the injured surface. The polymer swells in a damp environment, acting as a lubricant between the material.

The layered textile prepared according to this Example has additional advantages as a wound dressing, for example, because the layered textile maintains the air permeability of the material, which makes it possible to avoid a "hothouse" effect beneath the dressing/layer and the skin.

Example 3

Treatment of Wounds with Inventive Layered Textile Dressing

The present Example describes use of an inventive layered textile dressing in the treatment of patients in body cavity operations, parenchymatous bleeding contexts, or other surgical procedures.

Inventive layered textile dressings prepared according to Example 2 were tested for their hemostatic quality in the surgical division of the Russian State Medical University (RGMU). Pads (60×10 cm or 10×18 cm) were applied as a local hemostatic medium to halt bleeding from small vessels. 30 patients who had undergone body cavity operations or other surgical procedures, or who suffered from parenchymatous bleeding were treated. Pads were applied to the surface of a wound for 30-40 seconds, and resulting in the halting of the bleeding. No side effects in the application of pads were observed.

Additional clinical testing of inventive layered textile dressing has been performed at the I.M. Sechenov Moscow Medical Academy (MMA), the M. F. Vladimirsky Moscow Regional Scientific Research Clinical Institute (MONIKI), and the Scientific Research Institute of Laser Medicine (NII of Laser Medicine).

EQUIVALENTS

Those of ordinary skill in the art will appreciate that the foregoing has described certain preferred embodiments of the invention. Various modifications, changes, and substitutions to compounds, materials, or methods described herein may be made without departing from the spirit or scope of the present invention, whose boundaries are established only by the subject matter of the appended claims.

We claim:

1. A method of promoting hemostasis in a subject in need thereof comprising administering to a site of bleeding in the subject a composition comprising an extract of chamomile flowers and dioecious nettle leaves, and a biocompatible polymer,
   wherein the extract comprises chamomile components and nettle components in a ratio of about 0.2-5.0:1,
   wherein the biocompatible polymer is present at about 4.2% (w/v) of the extract, and
   wherein the biocompatible polymer is selected from one or more of agarose, agar, carrageen, alginic acid, alginate or other alginic acid derivative, a hyaluronate derivative, a polyanionic polysaccharide, chitin, chitosan, fibrin, a polyglycolide, a polylactide, a polycaprolactone, a dextran or copolymer thereof, polyvinyl pyrrolidone, a polyacrylate, a wax, a polyethylene-polyoxypropylene-block polymer, wool fat, poly(L-lactic acid), poly(DL-Lactic acid) copoly(lactic/glycolic acid), cellulose, a cellulose derivative, a glycol, polylactide-polyglycolide, polymethyldisiloxane, polylactic acid, and ethylene vinyl acetate.

2. The method of claim 1, wherein promoting hemostasis stops bleeding in less than 50 seconds.

3. The method of claim 1, wherein promoting hemostasis stops bleeding in 30-40 seconds.

4. The method of claim 1, further comprising applying pressure to the site of bleeding.

5. The method of claim 4, wherein the pressure is applied manually.

6. The method of claim 4, wherein pressure is applied by an adhesive or elastic bandage.

7. The method of claim 1, further comprising administering an additional therapeutic agent.

8. The method of claim 7, wherein the additional therapeutic agent is selected from the group consisting of an antimicrobial, an antibiotic, an antimyobacterial, an antifungal, an antiviral, a neoplastic agent, an agent affecting the immune response, an antithrombotic, an antihyperlipidemic agent, a cardiac drug, a thyromimetic or antithyroid drug, an adrenergic, an antihypertensive agent, a cholinergic, an anticholinergic, an antispasmodic, an antiulcer agent, a skeletal and/or smooth muscle relaxant, a prostaglandin, a general inhibitor of the allergic response, an antihistamine, a local anesthetic, an analgesic, a narcotic antagonist, an antitussive, a non-steroidal anti-inflammatory agent, a steroidal anti-inflammatory agent, an antioxidant, a vaso-active agent, a bone-active agent, an antiarthritic, or a vitamin.

9. The method of claim 1, wherein the biocompatible polymer comprises a hydrophilic polymer.

10. The method of claim 1, wherein the biocompatible polymer comprises alginic acid or alginate.

11. The wound dressing according to claim 1, wherein said biocompatible polymer comprises a hydrogel.

12. The method of claim 1, wherein the composition is formulated as a gel.

13. The method of claim 1, wherein the composition is incorporated into a dressing.

14. The method of claim 13, wherein the dressing comprises a textile material and the composition is applied on one surface of the textile material.

15. The method of claim 14, wherein the composition is applied to the dressing in a layer not less than 0.025 mm thick.

16. The method of claim 14, wherein the textile material comprises a woven or non-woven material.

17. The method of claim 16, wherein the textile material has been stitched with reinforced threads separated from one another by a distance within the range of 1.0-10.0 mm.

18. The method of claim 14, wherein the textile material is a 6×10 cm pad, a 10×18 cm pad, or a 60×10 cm pad.

19. A method of promoting hemostasis in a subject in need thereof comprising administering to a site of bleeding in the subject a composition comprising:
   an amount of a biocompatible polymer selected from the group consisting of agarose, agar, carrageen, alginic acid, alginate or other alginic acid derivative, a hyaluronate derivative, a polyanionic polysaccharide, chitin, chitosan, fibrin, a polyglycolide, a polylactide, a polycaprolactone, a dextran or copolymer thereof, polyvinyl pyrrolidone, a polyacrylate, a wax, a polyethylene-polyoxypropylene-block polymer, wool fat, poly(L-lactic acid), poly(DL-Lactic acid) copoly(lactic/glycolic acid), cellulose, a cellulose derivative, a glycol, polylactide-polyglycolide, polymethyldisiloxane, polylactic acid, and ethylene vinyl acetate, and
   an extract of chamomile flowers and dioecious nettle leaves, wherein the extract comprises chamomile components and nettle components in a ratio of about 0.2-5.0:1, and further wherein the chamomile components and nettle components are present at an amount within a range of about 0.3-0.9%, about 0.4-0.6%, about 0.5-0.55% or about 0.33-0.92% of the amount of the biocompatible polymer.

20. The method of claim 19, wherein promoting hemostasis stops bleeding in less than 50 seconds.

21. The method of claim 19, wherein promoting hemostasis stops bleeding in 30-40 seconds.

22. The method of claim 19, further comprising applying pressure to the site of bleeding.

23. The method of claim 22, wherein the pressure is applied manually.

24. The method of claim 22, wherein pressure is applied by an adhesive or elastic bandage.

25. The method of claim 19, further comprising administering an additional therapeutic agent.

26. The method of claim 25, wherein the additional therapeutic agent is selected from the group consisting of an antimicrobial, an antibiotic, an antimyobacterial, an antifungal, an antiviral, a neoplastic agent, an agent affecting the immune response, an antithrombotic, an antihyperlipidemic agent, a cardiac drug, a thyromimetic or antithyroid drug, an adrenergic, an antihypertensive agent, a cholinergic, an anticholinergic, an antispasmodic, an antiulcer agent, a skeletal and/or smooth muscle relaxant, a prostaglandin, a general inhibitor of the allergic response, an antihistamine, a local anesthetic, an analgesic, a narcotic antagonist, an antitussive, a non-steroidal anti-inflammatory agent, a steroidal anti-inflammatory agent, an antioxidant, a vaso-active agent, a bone-active agent, an antiarthritic, or a vitamin.

27. The method of claim 19, wherein the biocompatible polymer comprises a hydrophilic polymer.

28. The method of claim 19, wherein the biocompatible polymer comprises alginic acid or alginate.

29. The wound dressing according to claim 19, wherein said biocompatible polymer comprises a hydrogel.

30. The method of claim 19, wherein the composition is formulated as a gel.

31. The method of claim 19, wherein the composition is incorporated into a dressing.

32. The method of claim 31, wherein the dressing comprises a textile material and the composition is applied on one surface of the textile material.

33. The method of claim 32, wherein the composition is applied to the dressing in a layer not less than 0.025 mm thick.

34. The method of claim 32, wherein the textile material comprises a woven or non-woven material.

35. The method of claim 34, wherein the textile material has been stitched with reinforced threads separated from one another by a distance within the range of 1.0-10.0 mm.

36. The method of claim 32, wherein the textile material is a 6×10 cm pad, a 10×18 cm pad, or a 60×10 cm pad.

* * * * *

UNITED STATES PATENT AND TRADEMARK OFFICE
CERTIFICATE OF CORRECTION

| | | |
|---|---|---|
| PATENT NO. | : 9,011,901 B2 | Page 1 of 1 |
| APPLICATION NO. | : 13/720307 | |
| DATED | : April 21, 2015 | |
| INVENTOR(S) | : Natalia Dmitrievna Oltarshevskaya et al. | |

It is certified that error appears in the above-identified patent and that said Letters Patent is hereby corrected as shown below:

On the title page insert item (73),

-- Assignee: Linda Eastwood, Beverly Hills, CA (US) --

Signed and Sealed this
Twenty-second Day of December, 2015

Michelle K. Lee
*Director of the United States Patent and Trademark Office*